United States Patent [19]

Marugg et al.

[11] Patent Number: 4,883,826

[45] Date of Patent: Nov. 28, 1989

[54] TERTIARY AMINE-CONTAINING POLYOLS PREPARED IN A MANNICH CONDENSATION REACTION USING A MIXTURE OF ALKANOLAMINES

[75] Inventors: J. E. Marugg, Boerhaavelaan, Netherlands; Michael A. P. Gansow, Waedenswil, Switzerland; J. A. Thoen, Dommelstraat, Netherlands

[73] Assignee: The Dow Chemical Company, Midland, Mich.

[21] Appl. No.: 225,313

[22] Filed: Jul. 27, 1988

[51] Int. Cl.$^4$ ............................................. C08G 18/28
[52] U.S. Cl. ..................................... 521/164; 521/167
[58] Field of Search ................................ 521/164, 167

[56] References Cited

U.S. PATENT DOCUMENTS

| | | | |
|---|---|---|---|
| 3,297,597 | 1/1967 | Edwards et al. | 521/166 |
| 3,998,766 | 12/1976 | Kan et al. | 521/127 |
| 4,371,629 | 2/1983 | Austin | 521/115 |
| 4,383,102 | 5/1983 | McDaniel et al. | 528/107 |
| 4,487,852 | 12/1984 | Brennan | 521/167 |

Primary Examiner—Maurice J. Welsh
Assistant Examiner—L. Henderson

[57] ABSTRACT

Mannich polyols of low viscosity and reduced reactivity are prepared by condensing a phenolic compound with formaldehyde and a mixture of diethanolamine and at least one other alkanol amine. The condensation product is the alkoxylated to form a polyol which is particularly useful in preparing rigid polyurethane foam.

12 Claims, No Drawings

TERTIARY AMINE-CONTAINING POLYOLS PREPARED IN A MANNICH CONDENSATION REACTION USING A MIXTURE OF ALKANOLAMINES

BACKGROUND OF THE INVENTION

This invention relates to polyols containing one or more tertiary amine atoms, which are prepared in a Mannich condensation reaction to form a tertiary amine-containing intermediate which is subsequently alkoxylated.

Polyol precursor materials made by alkoxylating a Mannich condensation product (Mannich polyols) are known to be useful in preparing certain types of polyurethanes. Because these Mannich polyols contain tertiary nitrogen atoms, they are often auto-catalytic, i.e. are sufficiently reactive with isocyanate groups that they can be used to prepare polyurethanes with reduced levels of urethane catalysts, or even none at all. These Mannich polyols are typically of low equivalent weight, which makes them particularly suited to preparing rigid polyurethane foam, although their use as a crosslinker in semiflexible polyurethane foams is known as well. See U.S. Pat. No. 4,371,629.

The Mannich polyols used in polyurethane foams are prepared by alkoxylating a condensation product of phenol or a substituted phenol, formaldehyde, and diethanol amine. Such Mannich polyols are described, for example, in U.S. Pat. Nos. 3,297,597, 4,137,265 and 4,383,102, incorporated herein by reference. Although these Mannich polyols are useful in certain applications, such as in making high density spray foam, they are often too reactive to be useful in many other applications where their use might be otherwise beneficial. Another problem with many Mannich polyols is that they tend to be very viscous. This viscosity makes them very difficult to process in many types of commercial foam equipment.

Accordingly, it would be desirable to provide a Mannich polyol which is of lower reactivity than conventional Mannich polyols and which has a viscosity such that it can be processed on the equipment used in a wide range of applications.

SUMMARY OF THE INVENTION

In one aspect, this invention is a polyol prepared by alkoxylating a Mannich condensate of a phenolic compound, formaldehyde, and a mixture of diethanolamine and at least one other alkanolamine, wherein the weight ratio of diethanolamine to the other alkanolamine is from about 1:19 to about 19:1.

In another aspect, this invention is a polyurethane foam which is prepared by reacting a polyisocyanate with an active hydrogen-containing composition which comprises the Mannich polyol of this invention, in the presence of a blowing agent.

The Mannich polyol of this invention is characterized by having a surprisingly low viscosity, as compared to a Mannich polyol which is prepared using either diethanolamine or the other alkanolamine alone in the condensation reaction. In addition, it is of significantly lower reactivity than polyols prepared similarly, but using diethanolamine alone.

DETAILED DESCRIPTION OF THE INVENTION

The polyol of this invention is prepared by alkoxylating a Mannich condensation product, which is itself prepared in a process characterized by the use of a mixture of diethanolamine and a different alkanolamine as the amine reactant.

The Mannich condensation is well known in the art. It involves the reaction of a phenolic compound, formaldehyde and a primary or secondary amine. In this invention, the phenolic compound used is one having at least one phenolic hydroxyl group. Preferably, the phenolic compound contains substantially one hydroxyl group which is bound to a carbon in an aromatic ring. The phenolic compound may contain other substituents which do not undesirably react under the conditions of the Mannich condensation reaction, the subsequent alkoxylation reaction, or the preparation of polyurethanes from the final product. Among such substituent groups are alkyl, aryl, alkoxy, phenoxy, halogen, nitro and similar groups. Preferred substituent groups are halogen, particularly chlorine, and $C_1$–$C_{18}$, more preferably $C_1$–$C_{12}$ alkyl group(s). In addition to single ring phenolic compounds, fused ring compounds such as the various naphthols and hydroxyanthracenes are useful herein. Exemplary phenolic compounds include phenol, o-, p-, or m-cresols, ethylphenol, nonylphenol, dodecylphenol, p-phenylphenol, the various bisphenols including 2,2-bis(4-hydroxyphenyl)propane (bisphenol A), $\beta$-naphthol, $\beta$-hydroxyanthracene, p-chlorophenol, o-bromophenol, 2,6-dichlorophenol, p-nitrophenol, 4- or 2-nitro-6-phenylphenol, 2-nitro-6- or 4-methylphenol, 3,5-dimethylphenol, p-isopropylphenol, 2-bromo-6-cyclohexylphenol and the like. Preferred phenolic compounds include phenol and monoalkyl phenols, with para-alkyl phenols and phenol being more preferred. Phenol and para-n-nonylphenol are most preferred on the basis of ready availability and desirable properties.

The formaldehyde used is in any convenient form, with paraformaldehyde, trioxane, "inhibited" methanol solutions and the commonly available aqueous formalin solutions being exemplary. In commercial processes, the formaldehyde is preferably used as a concentrated aqueous solution, particularly as a 37% aqueous solution.

In this invention, the diamine used is a mixture of diethanolamine and another alkanolamine. This other alkanolamine is either a monoalkanolamine, in which the nitrogen atom is mono- or disubstituted, or a dialkanolamine which is characterized by having two alkanol groups attached to the nitrogen atom, with one of the alkanol groups being other than ethanol. The alkanol group on the monoalkanolamine is any which is unsubstituted or inertly substituted with primary or secondary hydroxyl-substituted groups having about 2 to about 12, preferably 2 to about 6, more preferably about 2 to about 4 carbon atoms. The monoalkanolamine can also contain an inert substituent on the nitrogen atom, such as $C_1$–$C_{12}$, preferably $C_1$–$C_6$, alkyl and/or aryl substitution. Examples of such suitable monoalkanolamines are methylethanolamine, ethylethanolamine, methylisopropanolamine, ethylisopropanolamine, methyl-2-hydroxybutylamine, phenylethanolamine, ethanolamine, isopropanolamine and the like.

While monoalkanolamines can be used, they provide a lower functionality than do dialkanolamines, and their use is therefore less preferred. The preferred dialkanolamines, other than diethanolamine, advantageously contain alkanol groups which, when not ethanol, are advantageously primary or secondary hydroxyl- substituted alkyl groups having from about 3 to about 12, preferably about 3 to about 6, more preferably about 3 to about 4 carbon atoms. Exemplary dialkanolamines used herein include diisopropanolamine, ethanolisopropanolamine, ethanol-2-hydroxybutylamine, isopropanol-2-hydroxybutylamine, isopropanol-2-hydroxyhexylamine, ethanol-2-hydroxyhexylamine, and the like. Of these, diisopropanolamine and ethanolisopropanolamine are preferred. Mixtures of the foregoing dialkanolamines can also be used.

The alkanolamine mixture contains the diethanolamine and other alkanolamine or mixture thereof in a weight ratio of about 1:19 to about 19:1, preferably about 1:9 to 9:1, more preferably about 1:5 to about 5:1, most preferably about 1:3 to about 3:1.

In conducting the Mannich reaction, the ratios of phenolic compound, formaldehyde and alkanolamine mixture can be varied somewhat to produce a condensate of a desired functionality. Phenolic compounds are typically susceptible to Mannich condensation at the positions ortho and para to the hydroxyl group. Thus, for a single ring phenolic compound, up to three potential condensation sites are present. Accordingly, the number of condensation reactions which occur on average per molecule during the Mannich reaction will depend to a great extent on the molar ratios of components. In this invention, a molar ratio of phenolic compound to formaldehyde of about 1:0.9 to about 1:3.5 is advantageously used. When it is desired to add only one (dialkanol)aminomethyl group, a ratio of closer to about 1:1 is preferred. Similarly, if an average of about two such groups are desired, a ratio of about 1:1.75 to about 1:2.5 is preferred. Likewise, a ratio of about 1:2.5 to about 1:3.5 is preferred when it is desired to add a average of more than two such groups. In this invention, it is preferred to add an average of about 1.5 to about 2.5, and more preferred to add an average of about 1.75 to about 2.25 (dialkanol)aminomethyl groups per molecule, and a molar ratio of phenolic compound to formaldehyde of about 1:1.75 to about 1:2.5 is most preferred.

The alkanolamine mixture is normally employed in roughly equimolar quantities with the formaldehyde, such as at a mole ratio of about 1 mole of formaldehyde to about 0.75 to about 1.5 moles of alkanolamine mixture.

In conducting the Mannich condensation reaction, the phenolic compound, formaldehyde and alkanolamine mixture are combined and permitted to react. It is preferred to first mix the phenolic compound and alkanolamine mixture, and then add the formaldehyde slowly so as to minimize the exotherm. However, it is also possible to prereact the formaldehyde and alkanolamine mixture, and then add this intermediate to the phenolic compound. Water is stripped from the reaction mixture during the reaction in order to drive the reaction toward completion.

In a preferred process, the formaldehyde is added, with stirring, to the mixture of phenolic compound and alkanolamines slowly in order to control the exotherm of the reaction. Suitably, the rate of addition is chosen in order to maintain a temperature of about 30° to about 100°, preferably about 50° to about 80°, more preferably about 60° to about 70° C. Following the formaldehyde addition, the mixture is maintained at an elevated temperature until the reaction is essentially complete. This can be determined by monitoring the water content of the mixture, as the condensation reaction produces water. As described below, in the usual processing, water is stripped from the reaction mixture as the reaction proceeds. As the reaction is completed, water is no longer produced, so when the water content becomes less than about 5% by weight, substantial completion of the reaction is indicated. The temperature is not especially critical, but is preferably below that temperature at which a substantial quantity of Novolac formation occurs, and is sufficiently high on the other hand to provide an economically feasible reaction rate. Temperatures of about 40° to about 100° C. are preferred, with about 50° to about 80° C. being more preferred, and 60° to about 75° C. being most preferred.

Following the completion of the condensation reaction, water is advantageously removed from the Mannich condensate. It is preferred to remove water under reduced pressure at a temperature of about 30° to about 100°, preferably about 60° to about 100°, more preferably about 80° to about 90° C. Water is advantageously removed until the Mannich condensate has a water content of less than about 5%, preferably less than about 1.5%, more preferably about 0.1 to about 1% by weight. Following removal of the water, it is preferred to further heat the condensate at about 50° to about 130° C., preferably about 100° to about 125° C. to further drive the reaction to completion.

It has been found that temperatures near the top of the ranges stated in the preceding paragraph, which are normally encountered near the end of the water removal step, tend to favor the formation of Novalacs and resoles. This in turn causes the product to be a mixture of monomeric and higher molecular weight compounds. Unfortunately, in such cases the composition of the mixture tends to vary from batch to batch. Applicants have found, however, that the Novolac and resole forming reactions can be substantially reduced when the Mannich condensate is "capped" with a portion of the cyclic aliphatic ether prior to stripping the final portions of the water. This capping is preferably done by reacting the Mannich condensate with an alkylene oxide in the substantial absence of a basic catalyst prior to reducing the water content thereof to below about 0.5%, more preferably prior to reducing the water content to below about 1% by weight. The reaction of up to about 1 mole of alkylene oxide per dialkanolamine group on the Mannich condensate proceeds readily at moderate temperatures, and is very effective in reducing Novolac and resole formation during subsequent water removal and alkoxylation steps.

The intermediate thus obtained preferably has a basicity of about 3.7 to about 7.1 meq/g, more preferably from about 4.1 to about 6.0 meq/g for a dicondensate. It preferably has a basicity of about 2.3 to about 5.8, more preferably about 2.8 to about 4.2 meq/g for a monocondensate. For a tricondensate, it preferably has a basicity of about 4.8 to about 7, preferably about 5.2 to about 6.5 meq/g. It further preferably has a water content of less than 5%, more preferably less than 1.5%, most preferably less than 1%.

The Mannich condensate is then alkoxylated to prepare the polyol of this invention. The alkoxylation is advantageously conducted to add an average of about 0.5 to about 25, preferably about 0.5 to about 5, more preferably about 0.5 to about 1.5, even more preferably about 0.75 to about 1.2 moles of alkylene oxide per hydroxyl group on the Mannich condensate. Most preferably, an average of about 1 to about 1.2 moles of alkylene oxide are added per hydroxyl group on the Mannich condensate.

The alkoxylation is advantageously conducted by reacting the hydroxyalkyl groups of the Mannich condensate with an alkylene oxide as is well known in the art. The phenolic hydroxyl group(s) may or may not be alkoxylated.

The alkylene oxide used herein is any compound having an cyclic ether group and which is unsubstituted or inertly substituted, i.e., has no substituent groups which undesirably react with the Mannich condensate or which undesirably react under the conditions encountered in forming a polyurethane from the alkoxylated Mannich condensate. The cyclic ether group is preferably an $\alpha,\beta$-oxirane, i.e., a three-membered cyclic ether ring. Preferred cyclic aliphatic ethers include those represented by the structure:

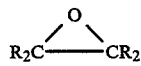

wherein each R is independently hydrogen or an unsubstituted or inertly substituted hydrocarbon group, including unsubstituted or inertly substituted alkyl, aryl or arylalkyl groups. Exemplary inert substituent groups include acyclic ether, nitro, halogen, particularly chlorine or bromine, and like groups. Particularly preferred alkylene oxides include ethylene oxide, propylene oxide, 1,2- or 2,3-butylene oxide, the various isomers of hexane oxide, styrene oxide, epichlorohydrin, epoxycyclohexane, epoxycyclopentane, and the like. Most preferred, on the basis of performance, availability and cost, are ethylene oxide, propylene oxide, butylene oxide, and mixtures thereof, with ethylene oxide, propylene oxide or mixtures thereof being most especially preferred.

The manner by which the alkoxylation reaction is conducted is not especially critical to the invention. The cyclic aliphatic ether is advantageously added to the Mannich condensate at an elevated temperature, such as about 50° to about 180°, preferably about 70° to about 160°, more preferably about 90° to about 150° C. In the usual case where a volatile cyclic aliphatic ether is used, the reaction is preferably conducted under superatmospheric pressure, although superatmospheric pressure is not particularly beneficial when a non-volatile cyclic aliphatic ether is used. A catalyst is also advantageously used to provide a commercially viable reaction rate. Any catalyst which enhances the rate of polymerization of alkylene oxides is useful herein. Examples of such catalysts include basic compounds such as alkali metal hydroxides, alkali metal alkoxides, alkaline earth alkoxides, alkali metal and alkaline earth naphthenates, tertiary amine compounds, and the like, including those described, for example, in U.S. Pat. Nos. 3,393,243 and 4,595,743, incorporated herein by reference. Alkali metal hydroxides are generally preferred. Suitable processes for reacting a Mannich condensate with a cyclic aliphatic ether are disclosed, for example, in U.S. Pat. Nos. 3,297,597, 4,371,629, and 4,137,265.

Following the polymerization of the cyclic aliphatic ether, the resulting Mannich polyol is advantageously worked up by removing unreacted alkylene oxide, such as by vacuum stripping, and by removing or deactivating any residual catalyst, such as by neutralization with a weak acid and/or filtration.

The polyol of this invention is of particular interest in preparing polyurethanes, especially rigid polyurethane or polyurethane-polyisocyanurate foam. In making such polyurethanes, the polyol of this invention is reacted with a polyisocyanate, optionally in the presence of a blowing agent, other isocyanate-reactive compounds, surfactants and other auxiliaries useful in producing polyurethanes.

Polyisocyanates useful in making polyurethanes include aromatic, aliphatic and cycloaliphatic polyisocyanates and combinations thereof. Representative of these types are diisocyanates such as m- or p-phenylene diisocyanate, toluene-2,4-diisocyanate, toluene-2,6-diisocyanate, hexamethylene-1,6-diisocyanate, tetramethylene-1,4-diisocyanate, cyclohexane-1,4-diisocyanate, hexahydrotoluene diisocyanate (and isomers), naphthylene-1,5-diisocyanate, 1-methylphenyl-2,4-phenyldiisocyanate, diphenylmethane-4,4'-diisocyanate, diphenylmethane-2,4'-diisocyanate, 4,4'-biphenylenediisocyanate, 3,3'-dimethoxy-4,4'-biphenylenediisocyanate and 3,3'-dimethyldiphenylpropane-4,4'-diisocyanate; triisocyanates such as toluene-2,4,6-triisocyanate and polyisocyanates such as 4,4'-dimethyldiphenylmethane-2,2',5',5'-tetraisocyanate and the diverse polymethylenepolyphenylpolyisocyanates.

A crude polyisocyanate may also be used in the practice of this invention, such as the crude toluene diisocyanate obtained by the phosgenation of a mixture of toluene diamines or the crude diphenylmethane diisocyanate obtained by the phosgenation of crude diphenylmethanediamine. The preferred undistilled or crude polyisocyanates are disclosed in U.S. Pat. No. 3,215,652, incorporated by reference.

Especially preferred are methylene-bridged polyphenylpolyisocyanates, due to their ability to crosslink the polyurethane. The isocyanate index (ratio of equivalents of isocyanates to equivalents of active hydrogen-containing groups) is advantageously from about 0.9 to about 10, preferably about 1.0 to about 4.0, more preferably about 1.0 to about 1.5.

In addition to the Mannich polyol and the polyisocyanate, various other components are useful in preparing polyurethanes. An additional isocyanate-reactive material, i.e., one which is not a Mannich polyol of this invention, may be employed in conjunction with the Mannich polyol of this invention. Preferably, the Mannich polyol constitutes at least about 20, more preferably at least about 50, most preferably at least about 70 weight percent of the combined weight of the Mannich polyol and the additional isocyanate-reactive material.

Suitable additional isocyanate reactive materials for preparing rigid polyurethanes include those having an equivalent weight of about 50 to about 400, preferably about 70 to about 200 and more preferably about 70–150. Such additional isocyanate-reactive materials also advantageously have a functionality of at least 3, preferably about 3 to about 8 active hydrogen atoms per molecule.

Suitable additional isocyanate-reactive materials include polyether polyols, polyester polyols, polyhydroxy-terminated acetal resins, hydroxyl-terminated amines and polyamines, and the like. Examples of these and other suitable isocyanate-reactive materials are described more fully in U.S. Pat. No. 4,394,491, particularly in columns 3–5 thereof. Most preferred for preparing rigid foams, on the basis of performance, availability and cost, is a polyether polyol prepared by adding an alkylene oxide to an initiator having from about 2 to about 8, preferably about 3 to about 8 active hydrogen atoms. Exemplary such polyols include those commercially available under the trade names Voranol® 250–473, Voranol® 240–360, Voranol® 270–370, Voranol® 240–446, Voranol® 240–490, Voranol® 575, Voranol® 240–800, all sold by The Dow Chemical Company, and Pluracol 824, sold by BASF Wyandotte.

In making the preferred rigid foam, a blowing agent is suitably employed to impart a cellular structure to the foam. Useful blowing agents include those materials which generate a gas under the conditions of the polymerization of the reaction mixture. Exemplary such materials include water, which reacts with isocyanate groups to liberate carbon dioxide, low boiling halogenated hydrocarbons such as fluorocarbons and fluorochlorocarbons, finely divided solids such as pecan flour, the so-called "azo" blowing agents which liberate nitrogen, and the like. Preferred blowing agents include water and the low boiling halogenated hydrocarbons. Water is particularly preferred in appliance and similar formulations, as it improves the flow properties of the formulation. When the polyurethane foam is desired to have thermal insulative characteristics, the blowing agent preferably comprises a low boiling halogenated hydrocarbon. Such blowing agents remain in the cells of the foam and contribute to the insulating properties thereof. Exemplary low boiling halogenated hydrocarbons include methylene chloride, tetrafluoromethane, trifluorochloromethane, dichlorodifluoromethane, CFC-142B, CFC-123, CFC-141B (all isomers) and the like.

Other auxiliaries useful in producing polyurethanes include surfactants, pigments, colorants, fillers, fibers, antioxidants, catalysts, flame retardants, stabilizers and the like. In making polyurethane foam, it is generally highly preferred to employ a minor amount of a surfactant to stabilize the foaming reaction mixture until it cures. Such surfactants advantageously comprise a liquid or solid organosilicone surfactant. Other, less preferred surfactants include polyethylene glycol ethers of long chain alcohols, tertiary amine or alkanolamine salts of long chain alkyl acid sulfate esters, alkyl sulfonic esters and alkyl arylsulfonic acids. Such surfactants are employed in amounts sufficient to stabilize the foaming reaction mixture against collapse and the formation of large, uneven cells. Typically, about 0.2 to about 5 parts of the surfactant per 100 parts by weight polyol are sufficient for this purpose.

One or more catalysts for the reaction of the polyol (and water, if present) with the polyisocyanate are advantageously used. Any suitable urethane catalyst may be used, including tertiary amine compounds and organometallic compounds. Exemplary tertiary amine compounds include triethylenediamine, n-methyl morpholine, pentamethyldiethylenetriamine, tetramethylethylenediamine, 1-methyl-4-dimethylaminoethylpiperazine, 3-methoxy-N-dimethylpropylamine, N-ethyl morpholine, diethylethanolamine, N-coco morpholine, N,N-dimethyl-N',N'-dimethyl isopropylpropylenediamine, N,N-diethyl-3-diethylaminopropylamine, dimethylbenzylamine and the like. Exemplary organometallic catalysts include organomercury, organolead, organoferric and organotin catalysts, with organotin catalysts being preferred among these. Suitable organotin catalysts include stannous chloride, tin salts of carboxylic acids such as dibutyltin di-2-ethyl hexanoate, as well as other organometallic compounds such as are disclosed in U.S. Pat. No. 2,846,408. A catalyst for the trimerization of polyisocyanates, such as an alkali metal alkoxide, may also optionally be employed herein. Such catalysts are used in an amount which measurably increases the rate of reaction of the polyisocyanate. Typical amounts are about 0.001 to about 1 parts of catalyst per 100 parts by weight of polyol.

In making a polyurethane foam, the polyol(s), polyisocyanate and other components are contacted, thoroughly mixed and permitted to expand and cure into a cellular polymer. The particular mixing apparatus is not critical, and various types of mixing head and spray apparatus are conveniently used. It is often convenient, but not necessary, to pre-blend certain of the raw materials prior to reacting the polyisocyanate and active hydrogen-containing components. For example, it is often useful to blend the polyol(s), blowing agent, surfactants, catalysts and other components except for polyisocyanates, and then contact this mixture with the polyisocyanate. Alternatively, all components can be introduced individually to the mixing zone where the polyisocyanate and polyol(s) are contacted. It is also possible to pre-react all or a portion of the polyol(s) with the polyisocyanate to form a prepolymer, although such is not preferred.

The polyurethane foam of this invention is useful in a wide range of applications, due to the desirable viscosity and reactivity of the Mannich polyol. Accordingly, not only can spray insulation be prepared, but appliance foam, rigid insulating boardstock, laminates, and many other types of rigid foam can easily be prepared with the Mannich polyol of this invention. Flexible foam is useful as, for example, cushioning material in mattresses, furniture, automobile seating and the like.

The following examples are given to illustrate the invention and are not intended to limit the scope thereof. Unless stated otherwise, all parts and percentages are given by weight.

EXAMPLE 1

The following general procedure is used to prepare Mannich condensates used in the following examples.

A 5 liter reactor is charged with 5 moles of nonylphenol and 10 moles of an alkanolamine or mixture thereof as indicated below. This mixture is heated to 50° C., and with continuous stirring 10 moles of formaldehyde are added dropwise as a 37% by weight aqueous solution. The resulting mixture is then stirred for 16 hours at a temperature of about 60°–70° C., and then heated to 100° C. for 2 hours. The resulting condensate is then stripped under vacuum (1–10 mbar) at 80°–100° C., until the water content of the condensate is <1000 ppm. The condensate is then heated to 110°–110° C. To the resulting condensate are then added 10 moles of propylene oxide under slight nitrogen pressure, while maintaining a temperature of about 100°–110° C. After a combined feed and cook-down time of four hours, 1000 ppm potassium hydroxide are added as a 50% aqueous solution, followed by an additional 10 moles of propylene oxide, still maintaining a temperature of 100°–110° C. After a total feed plus cook-down time of 10 hours, 1000 ppm formic acid are added at 100° C. to neutralize the catalyst, followed by removal of residual formic acid under reduced pressure.

Using the general procedure described above, three Mannich polyols according to the invention (Sample Nos. 1–3) and two comparative Mannich polyols (Comparative Samples A and B) are prepared. In Sample No. 1, the alkanolamine is a 3:1 molar mixture of diethanolamine (DEA) and diisopropanolamine (DIPA). In Sample No. 2, the alkanolamine is a 1:1 molar mixture of (DEA) and (DIPA). In Sample No. 3, the alkanolamine is a 1:3 molar mixture of (DEA) and (DIPA). In Comparative Samples A and B, the alkanolamines are DEA and DIPA, respectively. The viscosity, equivalent weight, basicity and reactivity of each of Samples 1–3 and Comparative Samples A and B are determined, and are as reported in Table 1 following.

TABLE 1

| Property | Sample or Comparative Sample | | | | |
|---|---|---|---|---|---|
| | A* | 1 | 2 | 3 | B* |
| moles DEA/mole nonylphenol | 2 | 1.5 | 1 | 0.5 | 0 |
| moles DIPA/mole nonylphenol | 0 | 0.5 | 1 | 1.5 | 2 |
| Viscosity, cst | 22,000 | 6,800 | 11,650 | 12,000 | 28,000 |
| Equivalent weight | 144 | 148 | 154 | 168 | 153 |
| Basicity, meq/g | 2.9 | 2.9 | 2.9 | 2.7 | 3.1 |
| Cream time, sec | 20 | 20 | 21 | 30 | 30 |
| Gel time, sec | 47 | 55 | 61 | 90 | 100 |
| tack free time, sec | 62 | 75 | 90 | 140 | 155 |

*Not an example of this invention.

Reactivity is measured by blending the materials listed in Table 2 following. The resulting mixture is then rapidly mixed at room temperature with a 2.7 functional polymeric MDI at a 1.1 index. The time elapsing from when the MDI is added until a visible reaction occurs is reported as the cream time. The time elapsing from when the MDI is added until the polymer forms strings when contacted with a spatula is reported as the gel time. The time elapsing from when the MDI is added until the polymer is tack-free is reported as the tack free time.

As can be seen from the data in Table 1, the Mannich polyols of this invention exhibit a markedly reduced viscosity compared to either of the Comparative Samples. In addition, Samples 1–3 all have a significantly lower reactivity, as measured by gel

TABLE 2

| Component | Parts by Weight |
|---|---|
| Mannich Polyol | 70 |
| Supplemental polyol ① | 25 |
| Glycerine | 5 |
| TCEP ② | 10 |
| DMCHA ③ | 1 |
| Water | 1 |
| Silicone Surfactant ④ | 1 |
| Refrigerant 11 | to provide 13.1% of combined weight of isocyanate and polyols |

① A tetrafunctional poly (propylene oxide) having a hydroxyl number of 490.
② trichloroethylphosphate
③ dimethylcyclohexylamine
④ B1049, sold by T. H. Goldschmidt time, cream time and tack free time, than Comparative Sample A. Other properties are not substantially changed.

EXAMPLE 2

Rigid polyurethane foams Samples 1–3 and Comparative Samples A and B are prepared using the formulation described in Table 2 in Example 1. The foams are processed on a Zaco PT I low pressure lab dispenser at a 1.1 index. The properties of the resulting foams are as indicated in Table 3 following. As can be seen from the data in Table 3, the foams of this invention have excellent properties generally comparable to those of the Comparative Samples.

TABLE 3

| Property | Sample or Comparative Sample | | | | |
|---|---|---|---|---|---|
| | A* | 1 | 2 | 3 | B* |
| Free Rise Density ① | 29.9 | 29.7 | 29.4 | 29.5 | 30 |
| Thermal Conductivity ② | 17.5 | 17.9 | 18.6 | 19.0 | 17.6 |
| DIN 4102-B2 ③ | 14 | 13.5 | 13 | 14 | 14 |
| Demold, 20 × 20 × 20 cm ④ | | | | | |
| 3 min | N.D. | 13.0 | 13.4 | 12.5 | N.D. |
| 4 min | 12.0 | 12.3 | 11.4 | 11.0 | 6.0 |
| Demold, 10 × 30 × 30 cm | | | | | |
| 3 min | N.D. | 6.5 | 6.6 | 5.2 | N.D. |
| 4 min | 5.0 | 5.5 | 6.0 | 8.0 | 4.0 |

*Not an example of this invention.
① kg/m3.
② mW/M° K.
③ Burn length in cm. on a standard vertical burn test.
④ Post demold expansion in mm of a molding of indicated dimensions after curing for specified time.

What is claimed is:

1. A polyurethane foam which is the reaction product of a reaction mixture comprising a polyisocyanate, a blowing agent and a polyol characterized in that the polyol is prepared by alkoxylating a Mannich condensate of (a) phenol or an inertly-substituted phenol, (b) formaldehyde, and (c) a mixture of (i) diethanolamine and (ii) at least one other alkanolamine, wherein the weight ratio of diethanolamine to the other alkanolamine is from about 1:19 to about 19:1.

2. The polyurethane foam of claim 1 wherein the alkoxylation comprises addition of from about 0.5 to about 25 moles of alkylene oxide per hydroxyl group on the Mannich condensate.

3. The polyurethane foam of claim 2 wherein the other alkanolamine is diisopropanolamine, ethanolisopropanolamine, ethanolamine or monoisopropanolamine.

4. The polyurethane foam of claim 1 wherein components (a) and (b) are used in a molar ratio of about 1:0.9 to about 1:3.5 in preparing the Mannich condensate.

5. The polyurethane foam of claim 4 wherein components (b) and (c) are used in a molar ratio of about 1:0.75 to about 1:1.5 in preparing the Mannich condensate.

6. The polyurethane foam of claim 5 wherein the polyol is prepared by alkoxylating the Mannich condensate with about 0.5 to about 5 moles of an alkylene oxide selected from the group consisting of ethylene oxide, propylene oxide, or mixtures thereof, per hydroxyl group of the Mannich condensate.

7. The polyurethane foam of claim 6 wherein the alkylene oxide is propylene oxide or a mixture of ethylene oxide and propylene oxide.

8. The polyurethane foam of claim 7 wherein the Mannich condensate is reacted with about one mole of alkylene oxide prior to reducing its water content below about 1 percent by weight.

9. The polyurethane foam of claim 6 wherein the ratio of components (a) to (b) is about 1:1.75 to 1:2.5.

10. The polyurethane foam of claim 9 wherein the Mannich condensate is alkoxylated with about 1 to about 1.2 moles of alkylene oxide per hydroxyl group on the condensate.

11. The polyurethane foam of claim 10 wherein the alkylene oxide is propylene oxide or a mixture of ethylene oxide and propylene oxide.

12. The polyurethane foam of claim 11 wherein the Mannich condensate is reacted with about one mole of alkylene oxide prior to reducing its water content below about 1 percent by weight.

* * * * *